US005755708A

United States Patent [19]

Segal

[11] Patent Number: 5,755,708
[45] Date of Patent: May 26, 1998

[54] MECHANICAL APPARATUS AND METHOD FOR DEPLOYMENT OF EXPANDABLE PROSTHESIS

[76] Inventor: Jerome Segal, 6132 Western Ave., Chevy Chase, Md. 20815

[21] Appl. No.: 647,696

[22] Filed: May 15, 1996

Related U.S. Application Data

[63] Continuation-in-part of Ser. No. 353,558, Dec. 9, 1994, Pat. No. 5,527,282, and Ser. No. 569,579, Dec. 8, 1995, Pat. No. 5,695,469.

[51] Int. Cl.⁶ .................................................. A61M 29/00
[52] U.S. Cl. ........................... 604/109; 604/53; 604/104; 606/194
[58] Field of Search ..................................... 604/104, 202, 604/53, 107, 106; 606/194

[56] References Cited

U.S. PATENT DOCUMENTS

| 4,572,186 | 2/1986 | Gould et al. | 104/105 X |
|---|---|---|---|
| 4,885,003 | 12/1989 | Hillstead | 604/107 X |
| 4,998,539 | 3/1991 | Delsenti | 606/194 X |
| 5,002,560 | 3/1991 | Machold et al. | 604/104 X |
| 5,195,984 | 3/1993 | Schatz | 604/104 X |
| 5,405,380 | 4/1995 | Glenotti et al. | 604/104 X |
| 5,456,667 | 10/1995 | Hem et al. | 604/104 X |

*Primary Examiner*—Michael Powell Buiz
*Assistant Examiner*—N. Kent Gring
*Attorney, Agent, or Firm*—Michael E. Klicpera

[57] ABSTRACT

A mechanical prosthesis deployment device for enlarging a flow passage of a vessel by delivering and deploying an expandable stent or prosthesis within an obstruction in the vessel. The prosthesis deployment device comprises a cylindrically shaped expansion member adapted to be disposed within the expandable prosthesis and includes a means engaged to the expansion member for altering the distance between the proximal end and the distal end of the expansion member thereby transforming the expansion member between a diametrically contracted configuration and a diametrically expanded configuration.

The present method comprises the steps of advancing the expansion member to the obstruction in a vessel and applying opposed forces on said expansion member in an axial direction to move the expansion member to an expanded configuration wherein the expansion member exerts radial force on said prosthesis and said prosthesis is expanded and implanted into the vessel.

Another method comprises the steps of advancing the expansion member to the obstruction in a vessel and applying opposed forces on said expansion member in an axial direction to move the expansion member to an expanded configuration wherein the expansion member exerts radial force on a previously deployed prosthesis and said prosthesis is further expanded and implanted into the vessel.

19 Claims, 6 Drawing Sheets

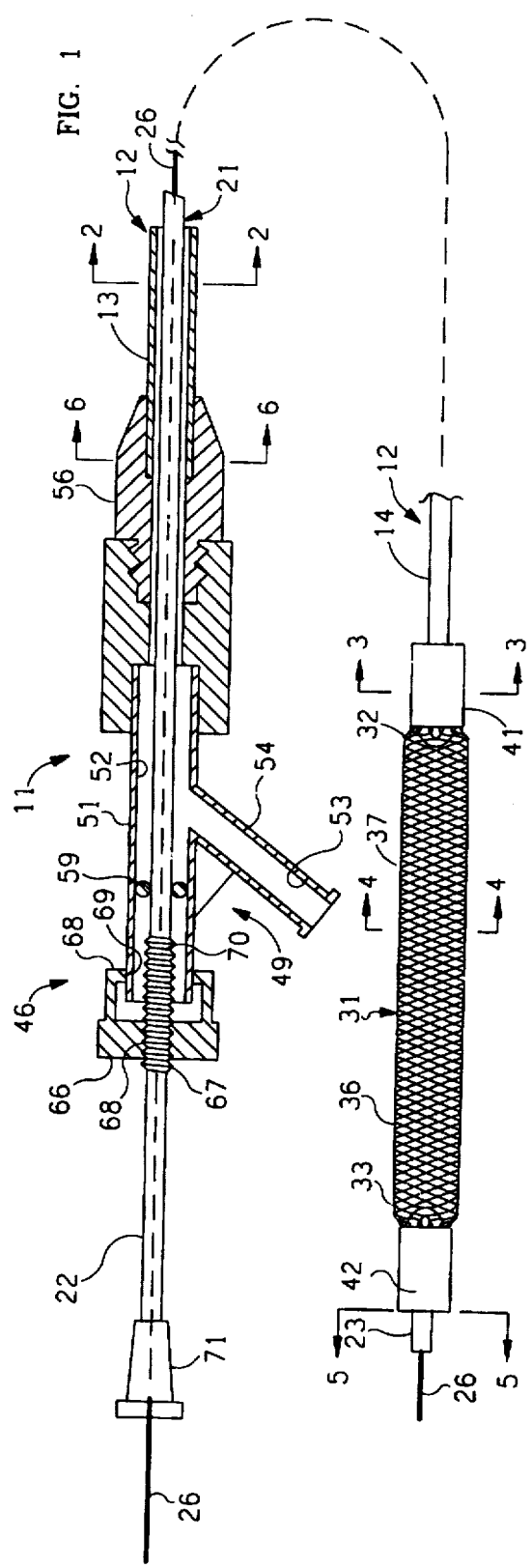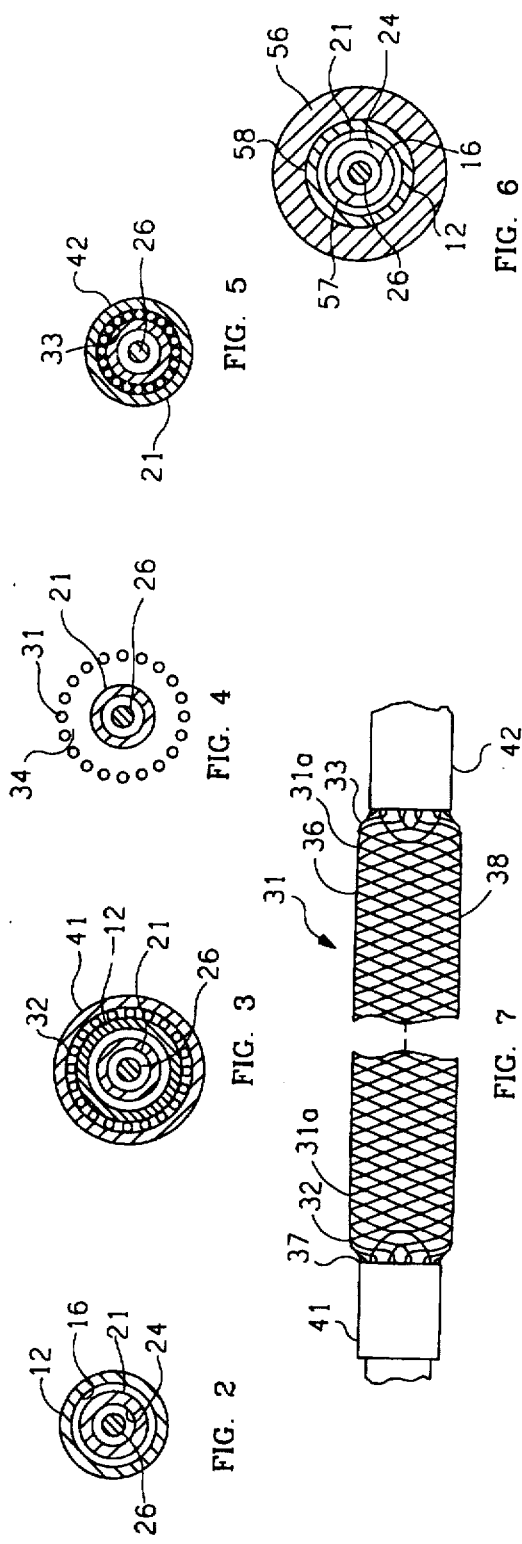

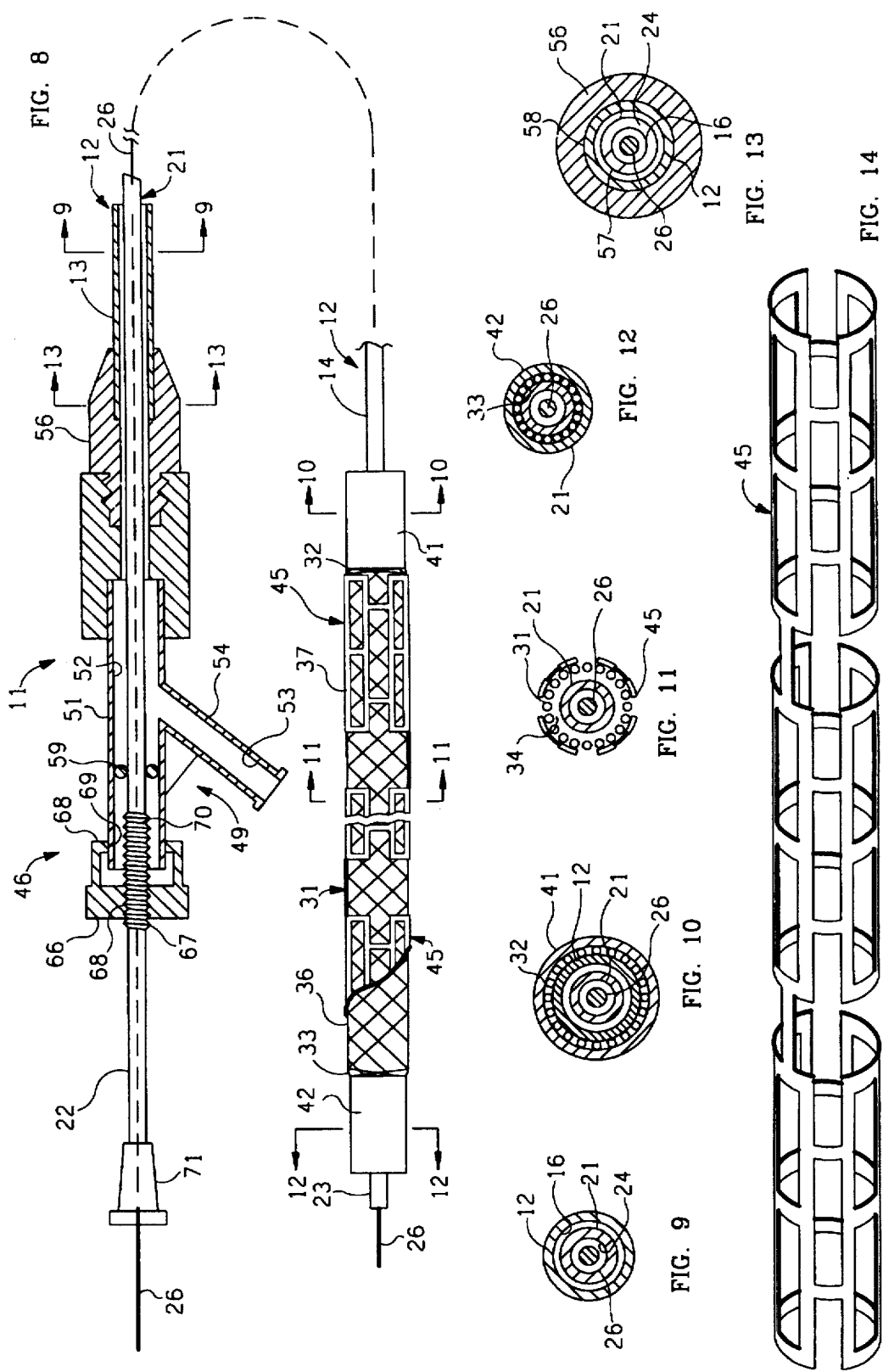

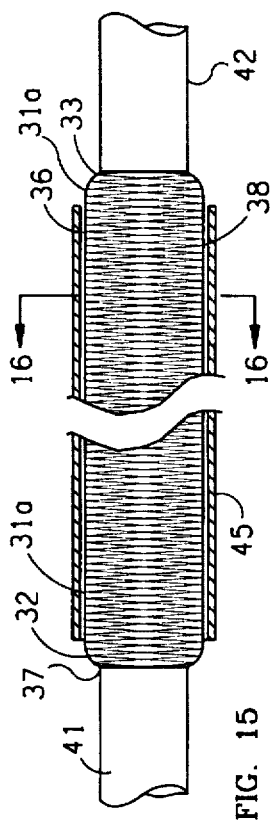
FIG. 15
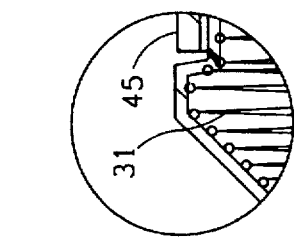
FIG. 16
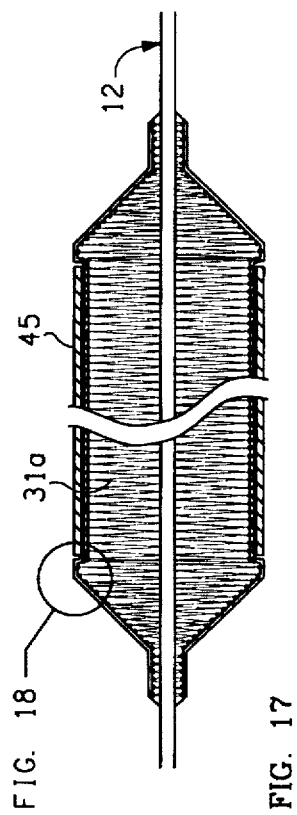
FIG. 17
FIG. 18
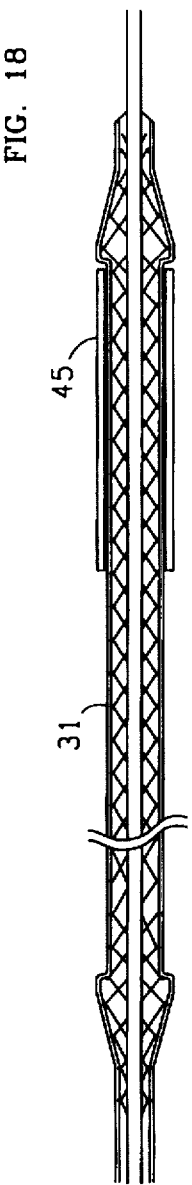
FIG. 19
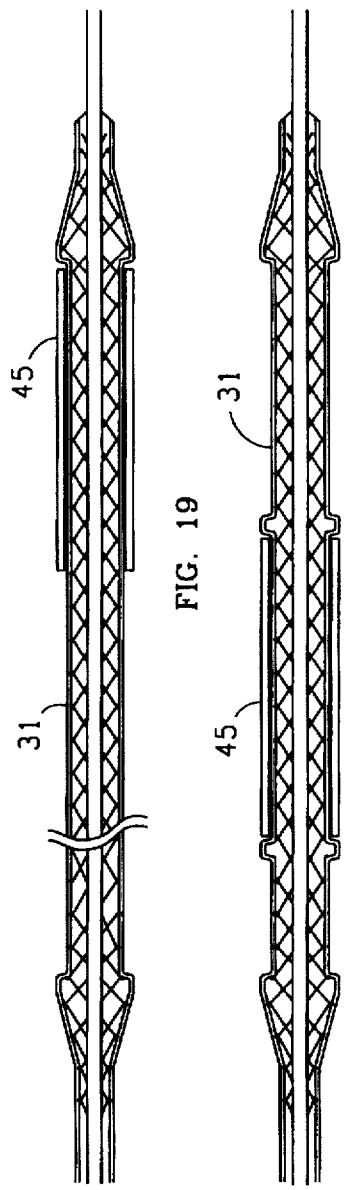
FIG. 20

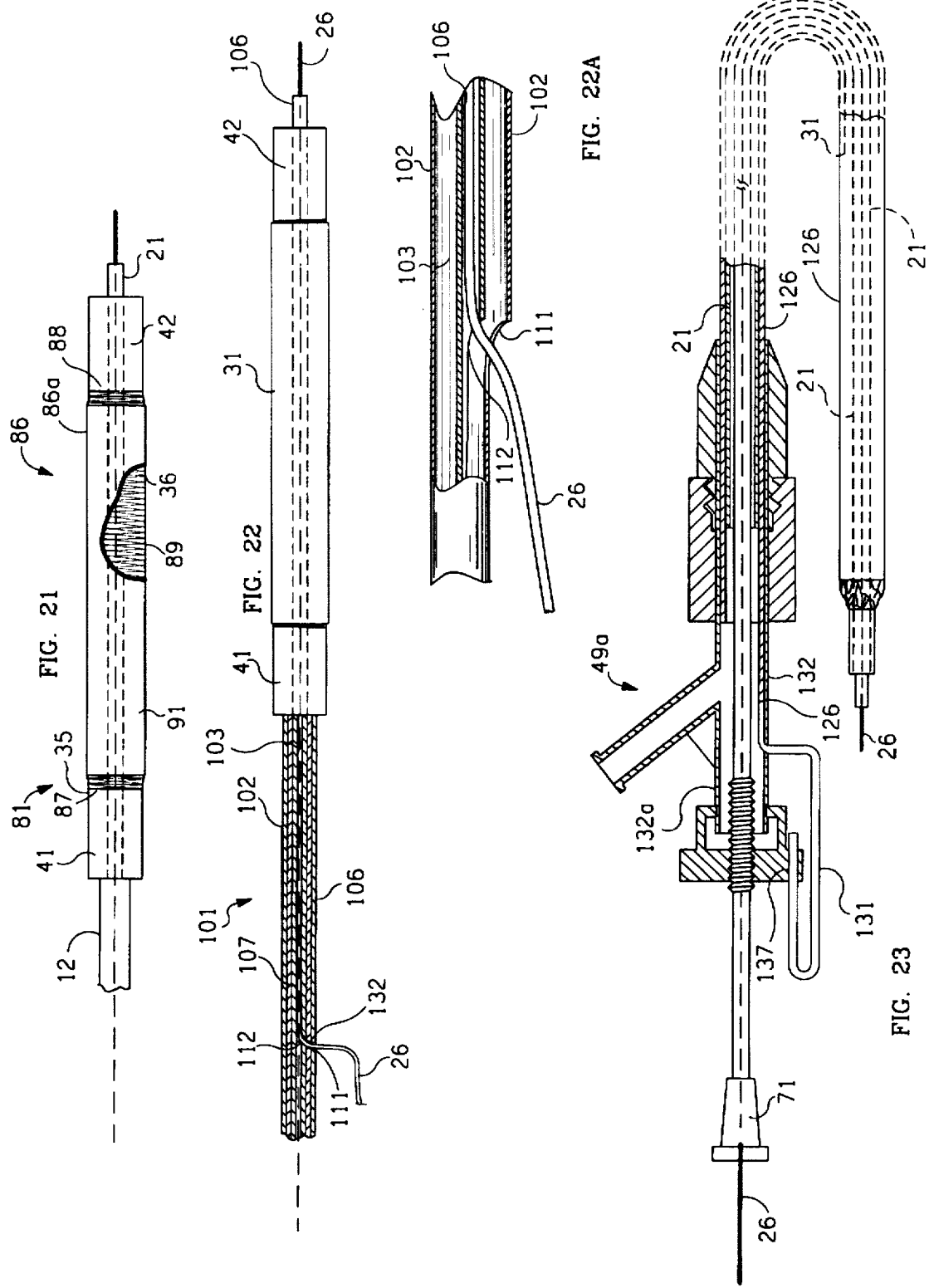

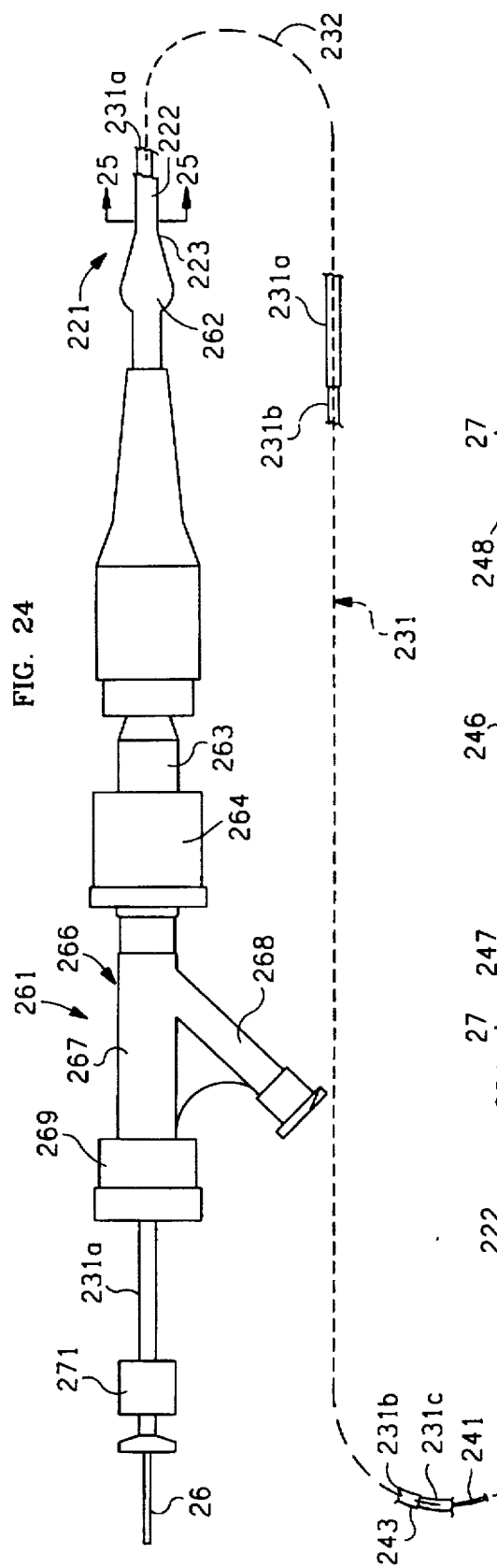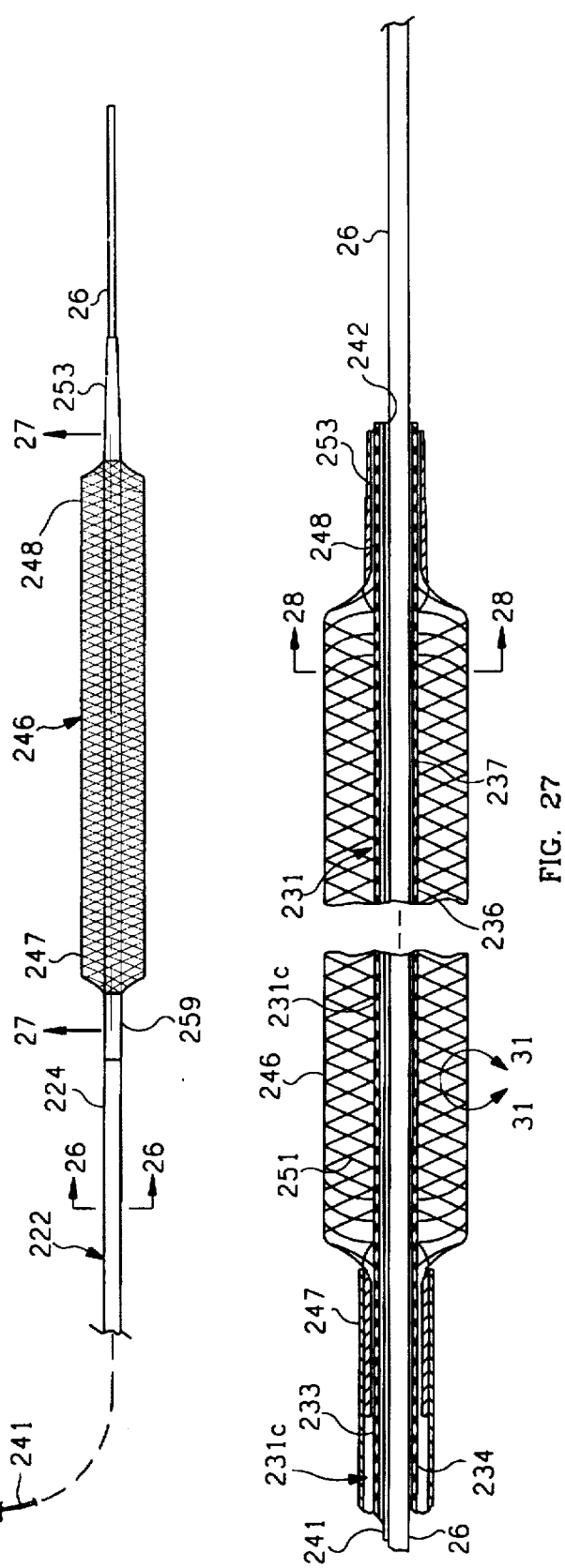

MECHANICAL APPARATUS AND METHOD FOR DEPLOYMENT OF EXPANDABLE PROSTHESIS

PRIOR APPLICATIONS

This application is a continuation-in-part of application Ser. No. 08/353,558 filed on Dec. 9, 1994 now U.S. Pat. No. 5,527,282 and a continuation-in-part of application Ser. No. 08/569,579 filed on Dec. 8, 1995 now U.S. Pat. No. 5,695,469. It was disclosed in both applications (page 29 lines 31 through 35 in the 08/353,558 and on page 29 lines 8 through 10 in the 08/569,579 application) that this invention could serve as a stent or prosthesis placement device.

FIELD OF THE INVENTION

In general, the present invention relates to percutaneous transluminal devices and methods which are used treat obstructed (sclerotic) vessel lumina in humans. In particular, this invention relates to a mechanical apparatus and method for percutaneous intraluminal delivery and deployment of an expandable or deformable stent or prosthesis at a selected site within a body passageway. Furthermore, the present invention permits a continuous flow of blood during the procedure.

BACKGROUND OF THE INVENTION

Cardiovascular disease is commonly accepted as being one of the most serious health risks facing our society today. Diseased and obstructed coronary arteries can restrict the flow of blood and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Open heart surgery is, of course, very traumatic for patients. In many cases, less traumatic, alternative methods are available for treating cardiovascular disease percutaneously. These alternate treatment methods generally employ various types of balloon (angioplasty) or excising devices (atherectomy) to remodel or debulk diseased vessel segments. A further alternative treatment method involves percutaneous, intraluminal installation of expandable, tubular stents or prostheses in sclerotic lesions.

Heretofore, balloon angioplasty catheters have been used to place and deploy a stent or prosthesis within human vessels. For example, in U.S. Pat. Nos. 4,733,665, 4,739,762, 4,776,337, 5,102,417, and 5,195,984, it is disclosed that an expandable and inflatable balloon catheter should be used to expand and deploy the claimed stent devices.

There are several disadvantages using balloon catheters to expand a deformable stent. First, there is the possibility of rupturing the balloon due to irregularities in the metal stent or prosthesis. Second, it is difficult to obtain symmetrical expansion of the stent because the radial force exerted by an expanded balloon varies along its entire axial length. This can leave portions of the stent or prosthesis not fully expanded or not completely attached to the vessel wall. Moreover, all angioplasty balloons are still somewhat compliant at their nominal working diameter, and they tend to expand beyond their nominal diameters as inflation pressure is increased. This characteristic of angioplasty balloons renders exact sizing of deployed stents or protheses variable and unpredictable because sizing is dependent upon the balloon's variable compliance. Third, during stent deployment during balloon expansion, bloodflow to the distal vessel is interrupted. This leads to tissue ischemia and potential necrosis.

Thus, it can be seen that there is a need for a new and improved stent or prosthesis delivery and deployment device and method which overcomes these disadvantages.

In general, it is an object of this present invention to provide a mechanical stent delivery and deployment device and method which will not be susceptible to structural damage due to its contact with irregularities on metal stents.

Another object of the invention is to provide a percutaneous device and method of the above character which can be used for prolonged periods in delivering and deploying stents or prostheses because it allows perfusion of blood into the vessel distal to the device.

Another object of the invention is to provide a device and method of the above character which can be used to expand deployed stents or prostheses to a predetermined, expanded size.

Another object of the invention is to provide a device and method of the above character in which the attribute of exerting constant radial forces along the entire axial length of the invention so that symmetrical expansion of the stent or prosthesis is ensured.

Another object of the invention is to provide a device and method of the above character which can employ radial force to further expand and implant stents or prostheses that previously were placed within a body passageway.

Another object of the invention is to provide a device and method of the above character which inhibits the attached stent or prosthesis from shifting, rotating or separating from the invention during delivery and deployment.

FIG. 1 is a side-elevational view partially in section of a mechanical prosthesis deployment device incorporating the present invention.

FIG. 2 is a cross-sectional view taken along the line 2—2 of FIG. 1.

FIG. 3 is a cross-sectional view taken along the line 3—3 of FIG. 1.

FIG. 4 is a cross-sectional view taken along the line 4—4 of FIG. 1.

FIG. 5 is a cross-sectional view taken along the line 5—5 of FIG. 1.

FIG. 6 is a cross-sectional view taken along the line 6—6 of FIG. 1.

FIG. 7 is a greatly enlarged view of a portion of the deployment device in a partially expanded state.

FIG. 8 is a side-elevational view of the mechanical prosthesis deployment device incorporating the present invention and showing the presence of the stent or prosthesis positioned on the device in its contracted state.

FIG. 9 is a cross-sectional view taken along the line 9—9 of FIG. 8.

FIG. 10 is a cross-sectional view taken along the line 10—10 of FIG. 8.

FIG. 11 is a cross-sectional view taken along the line 11—11 of FIG. 8.

FIG. 12 is a cross-sectional view taken along the line 12—12 of FIG. 8.

FIG. 13 is a cross-sectional view taken along the line 13—13 of FIG. 8.

FIG. 14 is an example of an expandable prosthesis or stent as represented in partial on FIGS. 8 and 11.

FIG. 15 is a side elevational view of a portion of the mechanical prosthesis deployment device showing the stent or prosthesis positioned on the device in a partially expanded state.

FIG. 16 is a cross-sectional view taken along the line 16—16 of FIG. 15.

FIG. 17 is a partial side-elevational view of another embodiment of the mechanical prosthesis deployment device showing the stent or prosthesis positioned on the device in its expanded state and demonstrating a prosthesis retention means shown here as raised shoulders on the proximal and distal ends.

FIG. 18 is a greatly enlarged view of the prosthesis retention means shown in FIG. 17.

FIG. 19 is a partial side-elevational view of the mechanical prosthesis deployment device in its contracted state showing the stent or prosthesis in a forward position and demonstrating the prosthesis retention means as raised shoulders on the proximal and distal ends.

FIG. 20 is a partial side-elevational view of the mechanical prosthesis deployment device in its contracted state showing the stent or prosthesis in a central position and demonstrating the prosthesis retention means as raised shoulders on the proximal and distal sides of the prosthesis.

FIG. 21 is a partial side-elevational view of another embodiment of a mechanical prosthesis deployment device incorporating the present invention with a part of the device covered by a protective material to prevent damage to the vessel wall.

FIG. 22 is a partial side-elevational view of another embodiment of a mechanical prosthesis deployment device incorporating the present invention which can be utilized in conjunction with a rapid exchange technique.

FIG. 22a is an enlarged side-elevational view of the rapid exchanged embodiment of the mechanical prosthesis deployment device demonstrating the guidewire entry ports in the inner and outer elongated tubular members.

FIG. 23 is a side-elevational view partially in section of another embodiment of a mechanical prosthesis deployment device incorporating the present invention which incorporates a retractable sleeve.

FIG. 24 is a side-elevational view partially in section of a mechanical deployment device incorporating another embodiment of the present invention.

FIG. 27 is an enlarged side-elevational view of a portion of the device shown in FIG. 18 looking along the line 27—27.

Figure 32:
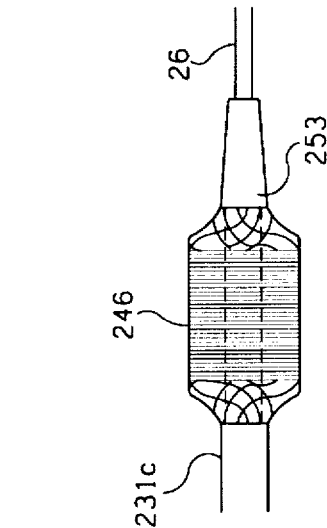
FIG. 32 is a side-elevational view of the distal extremity of the device shown in FIGS. 24-28 showing the distal extremity with the expansion member in an expanded condition.
Figure 28:
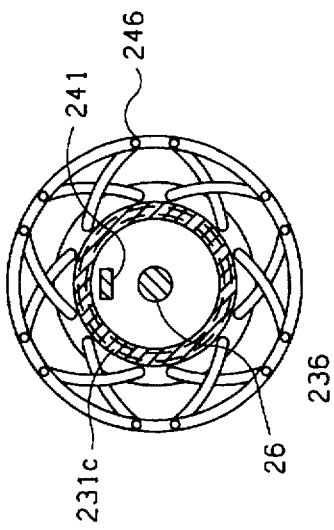
FIG. 28 is a cross-sectional view taken along the line 28—28 of FIG. 27.

In general, the present invention relates generally to devices which are used to deliver and deploy stents or prostheses within a stenotic segment of a vessel. The device is comprised of an expansion member adapted to be securely surrounded by an expandable stent or prosthesis that is deployed and implanted into a stenotic segment. The expansion member has first and second ends and an intermediate portion between the first and second ends. The expansion member also has a flow passage extending therethrough with a diameter and a longitudinal central axis. The diameter of the flow passage is a variable with movement of the first and second ends relative to each other along the longitudinal central axis from a diametrically contracted position to a diametrically expanded condition. The cylindrical expansion member is comprised of a plurality of flexible elongate elements each of which extends helically about the longitudinal extending central axis. A plurality of the flexible elongate elements having a first common direction of rotation are axially displaced relative to each other and cross a further plurality of the flexible elongate elements also axially displaced relative to each other but having a second common direction opposite to that of the first direction of rotation to form a braided cylindrical expansion member. The crossing of the flexible elongate elements occurs in an area of contact between the flexible elongate elements. First and second means is provided respectively engaging the first and second ends of said cylindrical expansion member for retaining said first and second ends in contracted positions. Means is provided for causing relative axial movement of the first and second ends towards each other to cause the intermediate cylindrical portion of the expansion member to contact longitudinally and to expand diametrically by causing the flexible elongate elements in the intermediate portion of the cylindrical member to move closer to each other expanding the diametric dimensions of the cylindrical expansion member thereby expanding the surrounding prosthesis within an obstruction in the vessel. Flexible elongate elements at the first and second ends of the cylindrical expansion member remain contracted around and within first and second means and are thereby prevented from moving closer which maintains spacing between the flexible elongate members so that blood in the vessel can continue to flow through the first and second ends and through the flow passage in the cylindrical expansion member while the cylindrical expansion member is in engagement with the prosthesis and obstruction in the vessel. Due to the interdigitated surface configuration of the expansion member interacting with the inner surface of the stent or prosthesis, frictional and some mechanical interlocking forces will be present to suppress the stent or prothesis from shifting axially, rotating, or separating from the expansion member.

More in particular as shown in FIGS. 1-7 of the drawings and also in FIGS. 8-14 of the drawings which show the presence of the prosthesis secured on the present invention, the mechanical prosthesis deployment device 11 shown therein consists of a first or outer flexible elongate tubular member 12 having proximal and distal extremities 13 and 14 with the flow passage 16 extending from the proximal extremity 13 to the distal extremity 14. A second or inner flexible tubular member 21 is coaxially and slidably disposed within the flow passage 16 of the first or outer flexible elongate tubular member 12 and is provided with proximal and distal extremities 22 and 23 with a flow passage 24 extending from the proximal extremity 22 to the distal extremity 23.

A guide wire 26 of a conventional type is adapted to be introduced through the flow passage 24 in the inner flexible elongate tubular member for use in guiding the mechanical prosthesis deployment device 11 as hereinafter described.

The guide wire 26 can be of a suitable size as for example 0.010"–0.035" and can have a suitable length ranging from 150 to 300 centimeters. For example, the first or outer flexible elongate tubular member 12 can have an outside diameter of 0.6–3 millimeters with a wall thickness of 0.12 millimeters to provide a flow passage of 0.75 millimeters in diameter. Similarly, the second or inner flexible elongate tubular member 21 can have a suitable outside diameter as for example 0.6 millimeters with a wall thickness of 0.12 millimeters and a flow passage 24 of 0.45 millimeters in diameter. The flexible elongate tubular members 12 and 21 can be formed of a suitable plastic as for example a polyimide, polyethylene, Nylon or polybutylterphalate (PBT).

In accordance with the present invention an expansion member 31 is provided which has a first or proximal end 32 and a second or distal end 33 with a central or inner flow passage 34 extending from the proximal end 32 to the distal end 33 along a longitudinally extending central axis and has a diameter which is a variable as hereinafter described. The expansion member 31 is comprised of a plurality of flexible elongate elements or filaments 36 each of which extends helically about the longitudinally extending central axis. The flexible elongate elements 36 are formed of suitable materials which can be utilized in the human blood as for example stainless steel, Nitinol, Aermet™, Elgiloy™ or certain other plastic fibers. The flexible elongate elements 36 can have a suitable diameter as for example 0.001 to 0.010 inches or can be configured as a round, elliptical, flat or triangular wire ribbon. A plurality of the flexible elongate elements 36 have a first common direction of rotation about the central axis as shown in FIGS. 1, 7, 8 and 15 are axially displaced relative to each other and cross a further plurality of the flexible elongate elements 36 also axially displaced relative to each other but having a second common direction of rotation opposite to that of the first direction of rotation to form a double helix or braided or mesh-like cylindrical expansion member with the crossing of flexible elongate elements 36 occurring in the area of contact between the flexible elongate elements to form openings or interstices 37 therebetween. Thus the flexible elongate elements 36 form an expansion member 31 which provides a central or inner flow passage 34 which is variable in diameter upon movement of the first and second ends of the expansion member 31 relative to each other along the longitudinally extending central axis. As shown in FIGS. 8, 11, and 15 through 20 of the drawings, an expandable stent or prosthesis 45 is intended to be placed on and secured to the expansion member 31.

Means is provided for constraining the first and second or proximal and distal ends 32 and 33 of the expansion member 31 and consists of a first or proximal collar 41 and a second or distal collar 42. The first and second collars 41 and 42 are formed of a suitable material such as a polyimide. The first or proximal collar 41 has a suitable length as for example 1.0 to 5.0 millimeters and is sized so that it can fit over the first or proximal end 32 of the expansion member 31 when it is in a contracted position and over the distal extremity 14 of the first or outer flexible elongate member 12. In order to ensure that elongate elements or filaments 36 of the first or proximal extremity 32 are firmly secured to the distal extremity 14 of the first or outer flexible elongate member 12, an adhesive can be provided bonding the first or proximal end 32 to the collar 41 and to the distal extremity 14 of the first or outer flexible elongate tubular member 12. The second or distal collar 42 can be of a suitable size and typically may be slightly smaller in diameter because it need merely secure the elongate element or filaments 36 of the distal end 33 of the expansion member 31 to the distal extremity 23 of the second or inner flexible elongate tubular member 21. An adhesive (not shown) is provided to firmly secure the second or distal end 33 of the expansion member 31 between the second or distal collar 42 and the distal extremity of the inner flexible elongate tubular member 21. In this manner it can be seen that the cylindrical expansion member 31 has its proximal end curved conically inward toward and secured to the distal extremity of the outer flexible elongate tubular member 12 and the second or distal end 33 of the expansion member 31 also curves conically inward toward and is secured to the distal extremity of the second or inner flexible elongate tubular member 21.

Typically the distance between the first and second collars 41 and 42 can range from between 5 to 150 millimeters. Typically the distal end 23 of the second or inner flexible elongate tubular member 21 extends approximately 5–170 millimeters beyond the distal extremity 14 of the first or outer flexible elongate tubular member 12.

It can be seen that by moving the first or outer flexible elongate tubular member 12 and the second inner flexible elongate tubular member 21 axially with respect to each other, the first and second ends of the expansion member 31 are moved towards each other causing the elongate elements or filaments 36 of an intermediate portion of the cylindrical expansion member between the first and second ends to move closer to each other to cause these flexible elongate elements to move into apposition with each other and to expand in a first radial direction the intermediate portion of the cylindrical expansion member 31 (FIGS. 7 and 15) and to cause the diameter of the central flow passage 34 to increase. As shown in FIG. 14, when the expansion member 31 expands in the first radial direction, it imparts radial forces on the surrounding prosthesis 45 causing it to expand to its predetermined diameter. The portions of the expansion member 31 immediately adjacent the first and second collars 41 and 42 remain restrained by the collars 41 and 42 causing the flexible elongate elements 36 immediately adjacent to the collars 41 and 42 to curve conically toward and remain crossed and unable to come into close apposition and thereby provide openings or interstices 37 therebetween, which remain relatively constant in shape and size so that blood can flow from the first and second ends 32 and 33 through the central or inner flow passage 34 as hereinafter described.

Means is provided in the mechanical prosthesis deployment device 11 for causing relative movement between the first or outer flexible elongate tubular member 12 and the second or inner flexible elongate tubular member 21 and consists of a screw mechanism 46. The screw mechanism 46 includes a Y-adapter 49 which is provided with a central arm 51 having a lumen 52 through which the second or inner flexible elongate tubular member 21 extends. The lumen or flow passage 52 is in communication with the lumen 16 of outer flexible elongate tubular member 12 and with a flow passage 53 in a side arm 54 which is adapted to receive a syringe (not shown) so that saline, radiocontrast liquid or a drug can be introduced through the side arm 54 and into the flow passage 52 in the Y-adapter 49 and thence into lumen 16 of outer member 12. The distal end of screw mechanism 46 is provided with a fitting 56 with inner lumen 57 (see FIGS. 6 and 13) into which the proximal end 13 of flexible elongate tubular member 12 is seated and held in place by an adhesive 58 at the distal end of fitting 56. Lumen 57 is thereby in communication with flow passage 52 of central arm 51 and with flow passage 53 of side arm 54. An 0-ring 59 which is adapted to form a fluid-tight seal with respect to the second or inner flexible tubular member 21 is disposed in the lumen 52 of the central arm 51. An interiorly threaded knurled knob 66 is threaded onto an exteriorly threaded member 67 which is secured to and surrounds the proximal extremity 22 of inner flexible elongate tubular member 21. The knob 66 is provided with an inwardly extending flange 68 which seats in an annular recess 69 in the central arm 51. Thus, rotation of the knob 66 causes advancement or retraction of threaded member 67 and the second or inner flexible elongate tubular member 21 with respect to the fitting 56. Indicia 68 in the form of longitudinally spaced-apart rings 70 are provided on the member 67 and serve to indicate the distance which the second or inner flexible elongate tubular member 21 has been advanced and retracted with respect to the first or outer flexible elongate member 12.

A Luer-type fitting 71 is mounted on the proximal extremity 22 of the inner elongate flexible tubular member 21 and is adapted to be engaged by a finger of the hand. The guide wire 26 extends through the fitting 71 and into the lumen 24 of inner elongate flexible tubular member 21. It should be appreciated that even though one particular screw mechanism 46 has been provided for advancing and retracting the flexible elongate members 12 and 21 with respect to each other, other mechanisms also can be utilized if desired to provide such relative movement. Other possible designs that could be employed are scissors-jack, rachet-type or straight slide mechanisms.

In order to provide the desired radiopacity for the distal extremity of the mechanical prosthesis deployment device 11 so that it can be observed fluoroscopically during a dilatation procedure, the collars 41 and 42 can be formed of a radiopaque material as for example by filling the polymeric material with radiopaque particles of a suitable material such as barium or by providing collars containing radiopaque metals, such as tungsten or platinum or a tungsten/platinum alloy. Although the flexible elongate elements 36 which comprise the expansion member 31 have some radiopacity by being formed of a stainless steel or other suitable material such as Elgiloy, there normally is insufficient radiopacity for most medical procedures. Therefore to augment the radiopacity of the expansion member 31, radiopaque wire of a suitable material such as platinum or tungsten can be wound along with the flexible elongate element 36 to provide the necessary radiopacity. This often may be desirable because this would make it possible to ascertain the position of the cylindrical expansion member and its diameter as it is expanded and retracted between a minimum contracted position and a maximum expanded position by relative movement between the distal extremities of the first or outer flexible elongate member 12 and the second or inner flexible elongate tubular member 21. The use of the helical wraps of platinum does not significantly interfere with the general mechanical properties of the expansion member 31 desired in connection with the present invention. Alternatively, the flexible elongate elements 36 may be plated with a radiopaque metal such as platinum or gold to enhance their radiopacity. Alternatively, the flexible elongate elements may be comprised of hollow wires, the central core of which may be filled with radiopaque metals such as tungsten, gold or platinum or with compound salts of high radiopacity.

Operation and use of the mechanical prosthesis deployment device 11 may now be briefly described as follows. Let it be assumed that the patient which the medical procedure is to be performed utilizing the mechanical prosthesis deployment device 11 has one or more stenoses which at least partially occlude one or more arterial vessels supplying blood to the heart and that it is desired to enlarge the flow passages through these stenoses. Typically the mechanical prosthesis deployment device 11 would be supplied by the manufacturer with the cylindrical expansion member 31 in its most contracted position to provide the lowest possible configuration in terms of diameter and so that the diameter approximates the diameter of the outer flexible elongate tubular member 12. Thus, preferably, it should have a diameter which is only slightly greater than the tubular member 12, as for example by 1.0–2.3 millimeters. The first and second collars 41 and 42 also have been sized so they only have a diameter which is slightly greater than the outer diameter of the outer flexible elongate tubular member 12. To bring the cylindrical expansion member 31 to its lowest configuration, the screw mechanism 46 has been adjusted so that there is a maximum spacing between the distal extremity 23 of the inner flexible elongate tubular member 21 and the distal extremity 14 of the outer flexible elongate tubular member 12. In this position of the expansion member 31, the flexible elongate elements 36 cross each other at nearly right angles so that the interstices or openings 37 therebetween are elongated with respect to the longitudinal axis.

With the screw mechanism 46 in this position, an expandable prosthesis or stent 45 will be placed over and surround the expansion member 31. As shown in FIGS. 18 through 20, a shoulder or retention means may be employed to restrict the prosthesis's longitudinal movement on the cylindrical member once the prosthesis is placed on the expansion member. In addition, a shoulder or retention means (not shown) can be adapted to the coated embodiment demonstrated in FIG. 21.

The mechanical prosthesis deployment device 11 is then inserted into a guiding catheter (not shown) typically used in such a procedure and introduced into the femoral artery and having its distal extremity in engagement with the ostium of the selected coronary artery. Thereafter, the guide wire 26 can be inserted independently of the mechanical prosthesis deployment device 11. If desired the guide wire 26 can be inserted along with the mechanical deployment device 11 with its distal extremity extending beyond the distal extremity of the mechanical prosthesis deployment device 11. The guide wire 26 is then advanced in a conventional manner by the physician undertaking the procedure and is advanced into the vessel containing a stenosis. The progress of the distal extremity of the guide wire 26 is observed fluoroscopically and is advanced until its distal extremity extends distally of the stenosis. With the expansion member 31 in its diametrically contracted position and the prosthesis secured thereon, the mechanical deployment device 11 is advanced over the guide wire 26. The distal extremity 23 of the second or inner flexible elongate tubular member 21 is advanced through the stenosis over the guide wire 26 until it is distal to the stenosis and so that the distal extremity 14 of the first or outer flexible elongate tubular member 12 is just proximal of the stenosis.

After the expansion member 31 is in a desired position in the stenosis, the expansion member 31 is expanded from its diametrically contracted position to an expanded position by moving the distal extremities 14 and 23 closer to each other by operation of the screw mechanism 46. This can be accomplished by holding one distal extremity stationary and moving the other distal extremity towards it or by moving both distal extremities closer to each other simultaneously. This movement of the distal extremities 14 and 23 causes collars 41 and 42 to move closer to each other and to cause the central flexible elongate elements 36 forming the double helix mesh of the intermediate portion 31a of the flexible cylindrical expansion member 31 to move relative to each other to progressively decrease the vertical crossing angle of the double helically wound flexible elongate elements 36 from approximately 140° to 170° in its extended state to 5° to 20° in its axially contracted state and to progressively change the interstices or openings 37 from diamond-shaped openings with long axes parallel to the central longitudinal axis of the catheter in its extended state to substantially square-shaped openings in its intermediately contracted state to elongate diamond-shaped interstices or openings with the longitudinal axes extending in directions perpendicular to the central longitudinal axis with the flexible elongate elements 36 coming into close apposition to each other while at the same time causing radial expansion of the expansion member and to progressively increase the diameter of the central flow passage 34. The enlargement of expansion member 31 in addition to being viewed fluoroscopically can also be ascertained by the indicia 68 carried by the threaded member 67.

During the time that the expansion member 31 is being expanded, it exerts radial forces against the stent or prosthesis 45, thereby expanding the stent or prosthesis against the stenosis. The prosthesis compresses against and becomes implanted within the wall of the vessel thereby enlarging the stenosis so that an increased amount of blood can flow through the vessel. The intermediate portion 31a of the expansion member 31 when fully expanded is almost a solid tubular ma s s which has significant radial strength to fully expand the stent or prosthesis. In addition, because of spring-like properties of the enlarged expansion member being comprised of helically wound flexible elongate elements 36, the expansion member 31 can conform t o a curve within the blood vessel while still exerting significant radial force to the stent or prosthesis and to make possible compression of the stenosis without tending to straighten the curve in the vessel which typically occurs with standard straight angioplasty balloon systems. Since the ends of the expansion member 31 are constrained by the proximal and distal collars 41 and 42, the flexible elongate elements 36 form a braided mesh of the expansion member 31 adjacent to the distal extremity 23 of the inner elongate flexible tubular member 21 and the distal extremity 14 of the outer flexible elongate tubular member 12 under the collars 41 and 42, respectively, are held in substantially constant angular relationship to each other with the vertical crossing angles between 5° and 170° and are unable to come into close apposition with each other. Therefore the interstices or openings 37 adjacent the collars 41 and 42 remain open because the flexible elongate elements 36 are unable to change from their relatively fixed crossed positions. Blood continues to flow through the central or inner flow passage 34 by passing through the openings 37 in the first or proximal end 32 into the central or inner passage 34 and out the openings in the second or distal end 33. Thus, blood flow through the vessel is not impeded by the expansion of the expansion member 31. It is believed that the flow through the central or inner flow passage 34 can be significantly greater than that which can be provided with a standard perfusion balloon.

Since blood flows continuously throughout the prosthesis deployment procedure, there is minimal danger of ischemia occurring. This makes it possible to maintain the dilatation and deployment of the prosthesis over extended periods of time when desired. One particularly advantage for prosthesis deployment with the mechanical deployment device 11 is that it could be used with patients which have obstructions of a critical nature that cannot even tolerate relatively short periods of balloon dilatation without leading to ischemia creating permanent damage or shock to the patient.

The open construction of the expansion member 31 also serves to prevent blocking off of other vessels branching off from the vessel in the region in which prosthesis deployment procedures are being performed because the blood can flow through the central interstices 38 of the expansion member 31.

After the dilatation and prothesis deployment has been carried out for an appropriate length of time, the expansion member 31 can be moved from its expanded position to a contracted position by operation of the screw mechanism 46 in a reverse direction to cause separation of the distal extremities 14 and 23 to thereby cause elongation of the expansion member 31 with a concurrent reduction in diameter.

After the expansion member 31 has been reduced to its contracted or minimum diameter, the mechanical prothesis deployment device 11 can be removed along with the guide wire 26 after which the guiding catheter (not shown) can be removed and the puncture site leading to the femoral artery closed in a conventional manner.

Although, the procedure hereinbefore described was for treatment of a single stenosis, it should be appreciated that if desired during the same time that the mechanical prosthesis deployment device 11 is within the guiding catheter, other vessels of the patient having stenoses therein can be treated in a similar manner merely by retracting the distal extremity of the mechanical prosthesis deployment device 11 from the stenosis being treated, placing another prosthesis over the expansion member, and then advancing it into another stenosis in another vessel in a similar manner.

Another embodiment of a mechanical prosthesis deployment device of the present invention is shown in FIG. 21 in which the mechanical prosthesis deployment device 81 is very similar to the mechanical deployment device 11 with the exception that the flexible cylindrical expansion member 86 is constructed in a different manner. As shown in FIG. 21, the flexible stainless steel expansion member 86 is formed of flexible elongate elements 36 in the manner hereinbefore described to provide a mesh construction having proximal and distal extremities 87 and 88 and having an intermediate portion 86a between the proximal and distal extremities 87 and 88 and a central flow passage 89 extending therethrough. The expansion member 86 differs from the expansion member 31 in that the outer surface of the intermediate portion 86a between the proximal and distal ends 87 and 88 carries and is covered or encapsulated with a radially expandable and contractible material 91 such as a latex, polyurethane, silicone or other thermoplastic elastomer. Such a flexible, expandable and contractible coating can be readily provided on the flexible cylindrical member 86 such as by placing the same on a mandrel (not shown) and masking off the proximal and distal extremities 87 and 88 by a suitable masking material and then dipping the expansion member into the desired coating material and then cured in an appropriate manner to bond the expandable-contractible material 91 to the flexible elongate elements 36. The coating material 91 applied encapsulates the flexible elongate elements 36 and fills in the interstices or openings 38 between the elements in the intermediate portion 86a. Alternatively, a tubular sleeve of the appropriate dimensions may be made from the latex, polyurethane, silicone or polymer material and then placed over the intermediate portion 86a of the cylindrical deployment member 86 to leave the proximal and distal extremities 87 and 88 exposed. These proximal and distal extremities 87 and 88 can be secured to the distal extremities 14 and 23 by the collars of 41 and 42 in a manner similar that hereinbefore described. A means (not shown) can be implemented on the device by thickening the coating or attaching an element forming a shoulder or flap on both sides of the expansion member to suppress the stent or prothesis from shifting axially, rotating, or separating from the expansion member.

A mechanical prosthesis deployment device 81 constructed in this manner can be used in the same manner as the mechanical prosthesis deployment device 11 and can be operated in the same manner. The coated intermediate portion 86a serves to protect the vessel wall from damage and prevents potential entrapment of tissue between the flexible elongate elements 36 as they are being compressed axially while still permitting the relative free passage of blood into proximal extremity 87 and into the central flow passage 89 and out distal extremity 89.

Another embodiment of a prosthesis deployment device incorporating the present invention is shown in FIGS. 22 and 22a. As shown therein, the mechanical deployment device 101 is constructed in a manner similar to the mechanical prosthesis deployment device 11 with the exception that it is provided with rapid exchange capabilities. This is accomplished by providing an outer flexible elongate tubular member 102 having a lumen 103 therein and an inner flexible elongate tubular member 106 having a lumen 107 which have the expansion member 31 secured thereto by the proximal and distal collars 41 and 42. The outer flexible elongate tubular member 102 is provided with a port or opening 111 into the corresponding lumen 103 and which is 13–60 centimeters from the distal extremity 32 of the expansion member 31. A corresponding port or opening 112 into corresponding lumen 107 is provided within the inner flexible elongate tubular member 106. These ports 111 and 112 are positioned so that when the expansion member 31 is in its expanded position with the distal extremities of the members 102 and 106 being in closest proximity to each other, the openings 111 and 112 are in registration with each other. In this position, the mechanical prosthesis deployment device 101 can be loaded onto the guide wire 16 by advancing the most proximal extremity of guide wire 26 first into lumen 107 of the distal extremity of the inner flexible elongate member 106 and then back through port or opening 112 and port 111 which are in registration and out of the flexible elongate tubular member 102. The expansion member 31 is next contracted from its diametrically expanded condition to a contracted condition by moving the distal extremities of outer and inner flexible elongate tubular members 102 and 106 further apart by operation of screw mechanism 46. This procedure is performed while maintaining a stable position of the external position of guide wire 26 in a constant position in relation to port 111. As the distal extremity of flexible tubular member 106 is moved further from the distal extremity of flexible elongate tubular member 102, port 112 will move out of registration with port 111 while maintaining guide wire 26 within lumen 107 and advancing the distal extremity of the flexible elongate tubular member 106 along the guide wire 26. In this diametrically contracted state of the expansion member 31, the mechanical prosthesis deployment device 101 may be advanced along guide wire 26 through the region of stenosis in the blood vessel and enlargement of expansion member 31 may occur using screw mechanism 46 in the manner previously described. Once prosthesis deployment has been completed, expansion member 31 can be diametrically contracted and the mechanical prosthesis deployment device 101 may be removed from the blood vessel and the guiding catheter by maintaining a stable position of guide wire 26 in relation to the blood vessel and retracting device 101 along guide wire 26 until the distal extremity of inner flexible member 106 exits the patient's body. The mechanical prosthesis deployment device 101 may now be rapidly exchanged with another mechanical deployment device 101 as for example, one having an expansion member 31 which can be increased to a larger diameter over a standard 175 to 185 centimeter length guide wire 26.

Still another mechanical deployment device 121 incorporating the present invention is shown in FIG. 23 which is very similar to the mechanical prosthesis deployment device 11 hereinbefore described with the exception that it is provided with a retractable sheath 126 which extends the entire length of the outer flexible elongate tubular member 12 and extends over the cylindrical expansion member 31 and prosthesis 45 to facilitate passage of the cylindrical expansion member 31 and prosthesis 45 into and through a blood vessel without damage to the blood vessel by the exposed flexible elongate elements 36 of the cylindrical expansion member 31. The retractable sheath 126 extends proximally and extends through the screw mechanism 46 and is provided with a hook-like member 131 which is slidably mounted in a slot 132 located along central arm 132a of screw adapter 49a. The hook-like member 131 can travel through a distance permitting retraction of the retractable sheath 126 from over the cylindrical expansion member 31 and prosthesis 45 so that it can be expanded in the manner hereinbefore described. If desired, the hook-like member 131 can be provided with a portion 131a which extends distally and extends through a hole 137 provided in the knob 66 to prevent rotation of the knob until the hook-like member 131 has been retracted to uncover the cylindrical expansion member 31 and prosthesis 45. This prevents rotation of the screw mechanism 46 and expansion of the cylindrical expansion member 31 until the retractable sheath 126 has been fully retracted. Thereafter, the mechanical deployment device 121 can be operated in a manner similar to that hereinbefore described.

Another embodiment of a mechanical prosthesis deployment device 221 incorporating the present invention is shown in FIGS. 24–30. As shown therein, the device 221 consists of a flexible elongate tubular member 222 having proximal and distal extremities 223 and 224. The flexible elongate tubular member 222 can be formed out of a suitable material such as a polyethylene or a polyimide.

A lumen 226 extends from the proximal extremity 223 to the distal extremity 224 and has a size which is the same as in the first or outer flexible elongate tubular member 12 hereinbefore described in connection with the previous embodiments. Thus, it can have a suitable size as for example 3–5 French. A second or inner flexible elongate tubular member 231 is provided which is slidably and coaxially disposed within the lumen 226. It is provided with proximal and distal extremities 232 and 233 with a lumen 234 extending from the proximal extremity 232 to the distal extremity 233. In the present embodiment of the invention, the inner flexible elongate tubular member 231 serves as a support member. The flexible elongate tubular member 231 is formed of three portions 231a, 231b and 231c with the first portion 231a being at the proximal extremity 232 and the second portion 231b extending from the proximal extremity 232 to the near distal extremity 233. The portion 231a is formed of a hypotube having an outside diameter of 0.010" to 0.042" and an inside diameter of 0.012" to 0.030"

to provide a wall thickness of 0.002" to 0.010". The portion 231a has a suitable length as for example 10–30 centimeters. The second portion 231b can be formed so that it has an outside diameter of 0.016" to 0.042" and an inside diameter of 0.012" to 0.030" to provide a wall thickness of 0.002" to 0.010". Thus it can be seen that the portion 231a has a greater wall thickness and provides additional stiffness and rigidity. A guide wire 26 of the type hereinbefore described is slidably disposed in the lumen 234. The lumen 234 in the flexible elongate tubular support member 231 is sized so that it can readily accommodate the guide wire 26. Thus, if a guide wire having a size 0.014" is used, the lumen 226 should have a diameter which is greater than 0.016" to 0.018".

Figure 30:
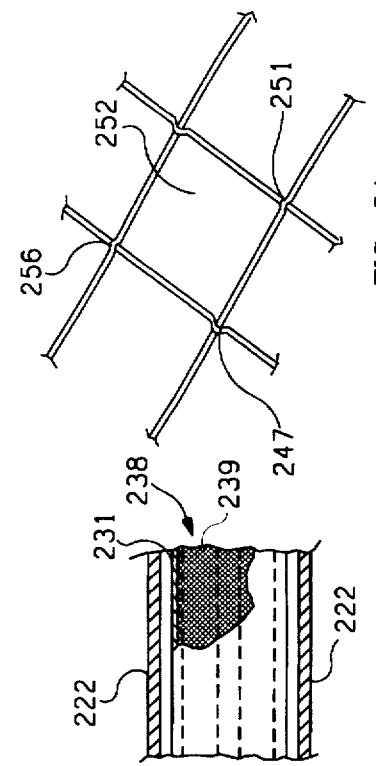
FIG. 30 is a cross-sectional view similar to FIG. 29 but showing the use of a braid rather than a coil spring.
Figure 25:
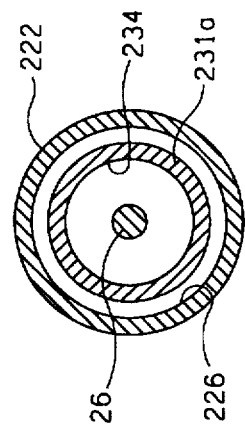
FIG. 25 is an enlarged cross-sectional view taken along the line 25—25 of FIG. 24.
Figure 29:
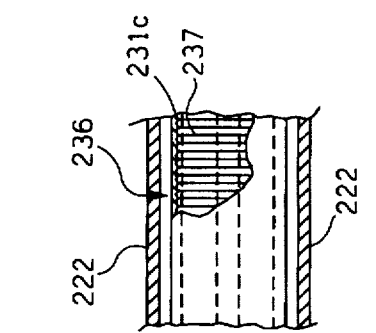
FIG. 29 is a cross-sectional view taken along the line 29—29 of FIG. 26.

The third portion 231c of the flexible elongate tubular support member 231 is formed of a suitable material such as plastic, as for example a polyimide. It has a suitable length, as for example from 20–40 centimeters and preferably a length of approximately 30 centimeters. The portion 231c is bonded to the distal extremity of the portion 231b by suitable means such as an adhesive. In order to increase the pushability of the portion 231c of the flexible elongate tubular member 231 while retaining its flexibility, a coil spring 236 is embedded within the plastic forming the portion 231c. The coil spring 236 is provided with a plurality of turns 237 as shown in detail in FIG. 29, which preferably are immediately adjacent or in apposition to each other to provide for maximum pushability. The coil spring 236 should extend at least throughout the length of the cylindrical deployment member 241 mounted coaxially thereover as hereinafter described. In addition, as shown the coil spring 236 can extend the entire length of the portion 231c. The coil spring 236 is carried by the portion 231c and preferably can be embedded or encapsulated within plastic 238 of the same type forming the tubular support member 231. Such embedding of the coil spring 236 prevents uncoiling of the coil elements or turns 237 and elongation of the flexible elongate tubular member 231 upon retraction of the inner elongate tubular member 231 into the outer elongate tubular member 226 with decrease in distance between proximal and distal ends of the expansion member 241. Alternatively, as shown in FIG. 30, a braided member 238 may be substituted for the coil spring 236 and also encapsulated or embedded with the plastic forming portion 231c. Such encapsulation also prevents elongation of portion 231c upon retraction of the flexible elongate tubular support member 231 into the outer elongate tubular member 226. The metal braid 238 formed of a suitable material such as stainless steel wires 239 of a suitable diameter ranging from 0.0002" to 0.003" can be used to form the mesh for the braided member 238. The braided member 238 increases the pushability of the portion 231c of the inner flexible elongate tubular member 231 and also prevents substantial elongation of the inner flexible elongate tubular member 231. Furthermore, metal braid 238 can consist of flat ribbon.

A safety ribbon 241 is provided within the inner flexible tubular member 231 to prevent elongation of the portion 231c of the inner flexible elongate tubular member 231 and extends from the distal extremity of portion 231b to the distal extremity of portion 231c. The safety ribbon 241 can be formed of a suitable material such as stainless steel having a diameter area of 0.002" to 0.004" or a ribbon with a flat cross section. The safety ribbon 241 is disposed adjacent the portion 231c of the flexible elongate tubular member 231, and preferably as shown extends interiorly of the portion 231c in the lumen 234 and has its distal extremity secured to the distal extremity of the portion 231c by solder 242. The safety ribbon 241 has its proximal extremity secured to the distal extremity of the portion 231b of the inner flexible elongate tubular member 231 by the use of solder 243 (see FIG. 24).

An expansion member 246 is provided with proximal and distal extremities 247 and 248 as shown in FIG. 27 and is disposed coaxially on the portion 231 of the inner flexible elongate tubular member 231. The expansion member 246 is constructed in a manner similar to the expansion member 31 hereinbefore described and is provided with a plurality of flexible elongate elements or filaments 251 in which a plurality of elements 251 have a first common direction of rotation about the central axis as shown in FIG. 24 and are axially displaced relative to each other and cross over a further plurality of the flexible elongate elements 251 also axially displaced relative to each other but having a second common direction of rotation opposite to that of the first direction of rotation to form a double helix, braided or mesh-like cylindrical expansion member 246 with the crossing of the flexible elongate elements 251 occurring in the area of contact between the flexible elongate elements 251 to form openings or interstices 252 therebetween. The solder 242 used for securing the safety ribbon 238 to the coil spring 236 is also used for securing the distal extremity 248 of the cylindrical deployment member 246 to the distal extremity of the inner flexible elongate tubular member 231. A sleeve 253 of heat shrink tubing covers the solder 242.

Figure 31:
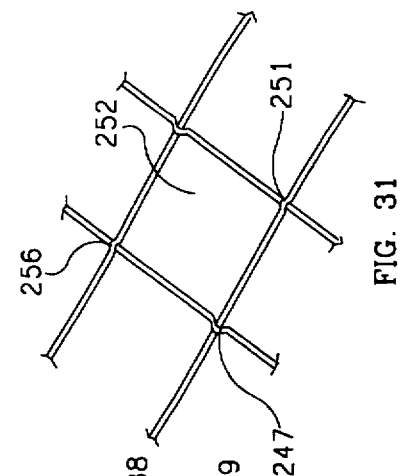
FIG. 31 is a greatly enlarged fragmentary view taken along the line 31—31 of FIG. 27.
Figure 26:
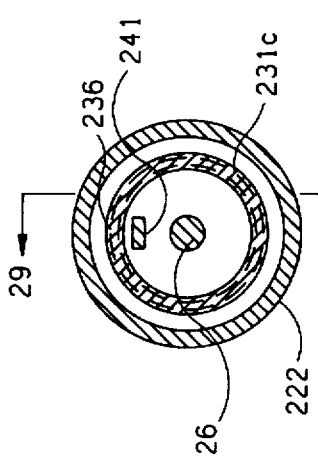
FIG. 26 is an enlarged cross-sectional view taken along the line 26—26 of FIG. 24.

In order to increase the radial forces generated by the expansion member 246, it has been found that it is desirable to provide undulations 256 in which there is an undulation 256 present at each cross-over point of the filaments 251. Thus, as shown in FIG. 31, which is a fragmentary view of the cylindrical expansion member 246 shown in FIG. 27, an undulation 256 is provided in each of the plurality of flexible elongate elements 251 having a first direction of rotation at every other cross-over point with the plurality of flexible elongate elements having a second common direction of rotation about the central axis and wherein the undulations in the adjacent elements 251 are offset by one crossover point so that in the resulting mesh or braid construction, the undulations 256 in one of the elements 251 having a first direction of rotation overlies every other cross-over point of the element 251 having a second direction of rotation and, conversely, every element 251 having a second direction of rotation has an undulation 256 therein at every other cross-over point of the elements 251 having a first direction of rotation. These undulations 256 can be in the form of obtuse angle bends having straight portions extending from both sides of the bend, or alternatively can be in the form of arcuate portions having a diameter corresponding generally to the diameter of the elements 251. Thus, it can be seen that the undulations 251 make it possible for one of the elements 251 to support the other of the elements at each crossover point, thereby preventing slippage of the elements 251 with respect to each other and thereby causing greater radial forces to be applied when the cylindrical expansion member 246 is expanded as hereinafter described. Furthermore, alternate braid configurations can be employed. One such alternate configuration is two wires crossing two wires alternatively (known as a 2 over 2 braid).

The expansion member 246 is comprised of 16–64 individual elements 251 formed of 0.001 to 0.005 inch diameter wire of a suitable metal such as stainless steel helically wound around a longitudinal central axis. The helices are wound in opposite directions. Stretching or elongation of the cylindrical expansion member 246 results in a reduction in diameter of the expansion member 246. Mechanical fixation of the proximal and distal extremities 247 and 248 of the expansion member 246 holds these extremities in reduced diameter configurations. The positions of the elements 251 in these extremities cannot change in relation to each other. Therefore, the crossing angles of the elements 251 remain constant. Shortening of the cylindrical deployment member 246 with the ends fixed results in the formation of a cylindrical center section of great rigidity with the elements 251 in close apposition to each other. The tapered proximal and distal extremities of the expansion member 246 causes the stresses on the individual elements 251 to be balanced. Since the proximal and distal extremities 247 and 248 are held in constant tapered positions, the interstices 252 between the elements 251 are maintained allowing blood to flow into and out of the cylindrical center section when the expansion member 246 is shortened as shown in FIG. 32. Shortening of the expansion member or spring 246 results in a significant increase in the metal density per unit length in the center portion of the expansion member 246 while the metal density at the ends is relatively constant. This increase in metal density in the center section results in significant radial force generation as the elements 251 are compressed in a longitudinal direction into preformed diameters.

Use of the helically wound coil spring 236 or the braid 238 which serves with or as part of the inner elongate tubular member 231 and coaxially disposed within the cylindrical expansion member 246 provides greatly improved pushability and axial column strength for causing elongation of the cylindrical expansion member 246 while providing the desired flexibility so that tortuous curves can be negotiated during deployment of the mechanical deployment device 221. The portion 231c of the flexible elongate tubular member 231, and particularly within the cylindrical expansion member 246, has a relatively small diameter so that it does not adversely affect the stenosis crossing profile for the mechanical prosthesis deployment device 221. The use of the inner or safety ribbon 241 prevents undue elongation and unwinding of the coil spring 236 forming a part of portion 231c of the flexible elongate tubular member 231 when the cylindrical expansion member 246 is lengthened or elongated. The pull or safety ribbon 241 also limits elongation of the cylindrical expansion member 246 and thereby prevents the elements 251 from being broken off or pulled away from the solder joints 253.

The proximal extremity 223 of the outer flexible elongate tubular member 222 of the mechanical prosthesis deployment device 221 is provided with control means 261 for causing relative movement between the first or outer flexible elongate tubular member 222 and the second or inner flexible elongate tubular member 231 and can be similar to that hereinbefore described. This control means 261 consists of a fitting 262 which is bonded to the proximal extremity 223 of the outer flexible elongate tubular member 222. The fitting 262 is provided with a male Luer fitting 263 removably mated with a female Luer fitting 264 carried by a Y-adapter 266 which is provided with a central arm 267 and a side arm 268. The side arm 268 is in communication with the lumen 226 of the outer flexible elongate tubular member 222. The inner flexible elongate tubular member 231 extends through the central arm 267 of the y-adapter 266. A rotatable knob 269 is provided on the central arm of the y-adapter 266 for forming a fluid-tight seal between the central arm 267 and the portion 231a of the inner flexible elongate tubular member 231. A male Luer fitting 271 is mounted on the proximal extremity of the portion 231a. The guide wire 26 extends through the lumen 234 of the inner flexible elongate tubular member 231 and extends beyond the distal extremity there of.

As hereinbefore described, the control means 261 can include means such as a screw mechanism for causing relative movement between the outer flexible elongate tubular member 222 and the inner flexible elongate tubular member 231.

Operation and use of the mechanical prosthesis deployment device 221 is substantially similar to that hereinbefore described with respect to the previous embodiments. The mechanical prosthesis deployment device 221 however has a number of features which may be more advantageous in certain medical procedures. Thus in medical procedures where improved pushability and torquability is required the use of the metal hypotube for the portion 231b of the flexible elongate tubular member provides additional pushability and torquability for the catheter facilitating advancement of the mechanical prosthesis deployment device 221 through more difficult stenoses, particularly where additional torquability and pushability are desired. This is also true with the distal extremity of the mechanical prosthesis deployment device 221 in which the inner flexible elongate tubular member 231 has the distal portion 231c thereof that includes the compressed coil spring 236 or braided member 238 which extends at least through the expansion member 246 to provide additional pushability for the expansion member 246 while still retaining the desired flexibility. Even though improved pushability is provided, the distal extremity of the mechanical deployment device 221 is still very flexible permitting it to track tortuosities in the vessels being negotiated thereby. Al so because of the pushability of the inner flexible elongate tubular member 231, it is possible to obtain maximum extension of the expansion member 246 and thereby a minimum diameter to facilitate crossing of a stenosis with very small openings therethrough with the mechanical prosthesis deployment device 221. The safety ribbon 241 prevents undue elongation of the inner flexible elongate tubular member 231. In addition, encapsulation of the compressed coil spring 236 or braided member 238 also prevents elongation of the inner flexible elongate tubular member 231.

When the expansion member 246 is being expanded by decreasing the length of the same, such as in the manner shown in FIG. 31, the diameter of the expansion member is increased to its maximum size with great rigidity because of the undulations 256 provided in the elements 251 of the expansion member 246. These undulations 256 aid providing greater radial forces while still retaining the conical or tapered ends with the open interstices to readily permit blood to pass through the expansion member 246 during the time that the expansion member 246 has been expanded to its maximum diameter to apply maximum radial forces to the stenoses which is being dilated during the procedure.

From the foregoing, it can be seen that there has been provided a mechanical prosthesis deployment device which can be used in the same manner as a balloon catheter in deploying a stent or prosthesis during an interventional procedure with the outstanding advantage that blood can continue to flow to the distal blood vessel during the procedure. This permits a longer vessel dilatation and stent or prosthesis deployment without tissue ischemia. In addition, perfusion of side branches continues through the flexible cylindrical member. Furthermore, the mechanical prosthesis deployment device also provides the advantages of known expanded non-compliant diameter and therefore exact sizing of the expanded stent or prosthesis. In addition, there is no possibility of a balloon rupture due to protrusions from the surface of the stent or prosthesis perforating the balloon during deployment.

5,755,708

What is claimed:

1. A device for intraluminal delivery and deployment of a stent or prosthesis positioned within a body passageway and enlarging a flow passage in a vessel carrying flowing blood which comprises:

a substantially cylindrical shaped expansion member having a first end and a second end, said first end being a distance from said second end;

an altering means engagable to said first end and said second end of said expansion member for altering said first distance therebetween to move said expansion member between a first configuration wherein said expansion member is characterized by a first diameter and a second configuration wherein said expansion member is characterized by a second diameter, said second diameter being greater than said first diameter;

said expansion member having an interior flow passage extending therethrough with a diameter and a longitudinally extending central axis for permitting the passage of blood through said expansion member; and said altering means including an outer flexible elongate tubular member having proximal and distal extremities, said distal extremity of the outer flexible elongate tubular member being secured to the first end of said expansion member and an inner flexible elongate tubular member having proximal and distal extremities and having sufficient rigidity for causing elongation of the expansion member, said distal extremity of the inner flexible elongate tubular member being secured to the second end of said expansion member.

2. A device as recited in claim 1 wherein said expansion member comprises a first plurality of flexible elongate elements helically wound in a first direction of rotation and a second plurality of flexible elongate elements helically wound in a second direction of rotation to form a braid.

3. A device as recited in claim 2 wherein each flexible elongate element has a circular cross section defined by a diameter and said diameter is in a range of approximately 0.001 to 0.010 inches.

4. A device as recited in claim 1 further comprising a coating, said coating being placed on said expansion member.

5. A device as recited in claim 4 wherein said coating is polyurethane.

6. A device as recited in claim 4 wherein said coating is silicone.

7. A device as recited in claim 1 further comprising a retaining means for maintaining said stent or prosthesis in a fixed position on said expansion member prior to expanding said prosthesis within said body passageway.

8. In combination with an expandable stent or prosthesis, a device for deploying an expandable stent or prosthesis positioned within a body passageway which comprises:

a cylindrical shaped expansion member adapted to be disposed within said expandable stent or prosthesis, said expansion member having a proximal end and a distal end, said proximal end being a distance from said distal end;

a means engaged to said proximal end and said distal end for altering said distance between said proximal end and said distal end of said expansion member, said altering means capable of transforming said expansion member between a first configuration wherein said expansion member is characterized by a first diameter and a second configuration wherein said expansion member is characterized by a second diameter, said second diameter being greater than said first diameter;

an elongated outer tubular member, said outer tubular member having a proximal end and a distal end, said outer tubular member formed with a lumen which extends longitudinally therein over essentially the entire length thereof, said proximal end of said expansion member engaged with said distal end of said outer tubular member; and an elongated inner tubular member coaxially disposed within said outer tubular member, said inner tubular member having a proximal end and a distal end, said proximal end of the inner tubular member engaged with said proximal end of said outer elongated tubular member and said distal end of said inner tubular member connected to said distal end of said expansion member.

9. A device as recited in claim 8, wherein said inner tubular member is formed with a lumen which extends longitudinally therein essentially the entire length thereof, for receiving a guidewire.

10. In combination with an expandable stent or prosthesis, a device for intraluminal delivery and deployment of an expandable stent or prosthesis positioned within a body passageway which comprises:

a cylindrical shaped expansion member adapted to be disposed within said expandable prosthesis having a proximal end and a distal end, said proximal end being a distance from said distal end;

a means for altering said distance between said proximal end and said distal end of said expansion member, said altering means capable of transforming said expansion member between a first configuration wherein said expansion member is characterized by a first diameter and a second configuration wherein said expansion member is characterized by a second diameter, said second diameter being greater than said first diameter;

an elongated outer tubular member, said outer tubular member having a proximal end and a distal end, said outer tubular member formed with a first lumen which extends longitudinally therein over essentially the entire length thereof, said first lumen being continuous with a first opening located within said outer tubular member, said first opening located near said distal end of said outer tubular member, and said proximal end of said expansion member engaged with said distal end of said outer tubular member; and an elongated inner tubular member coaxially disposed within said outer tubular member, said inner tubular member having a proximal end, a distal end and a distal portion, said inner tubular member formed with a second lumen for receiving a guidewire which extends longitudinally therein over said distal portion thereof, said second lumen continuous with a second opening located within said distal portion of said inner tubular member, said proximal end of said inner tubular member engaged with said proximal end of said outer tubular member, and said distal end of said inner tubular member engaged with said distal end of said expansion member.

11. In combination with an expandable stent or prosthesis, a device for intraluminal delivery and deployment of a stent or prosthesis positioned within a body passageway which comprises:

an expansion member for carrying said stent or prosthesis, said expansion member being moveable between a first configuration wherein said member is defined by a first dimension extending in a radial direction, and a second configuration wherein said member is defined by a second dimension extending in said radial direction; and means for applying opposed forces on said expansion member in an axial direction to move said expansion member between said first configuration and said second configuration;

said expansion member having an interior flow passage extending therethrough with a diameter and a longitudinally extending central axis for permitting the passage of blood through said expansion member; and said means for applying opposed forces including an outer flexible elongate tubular member having proximal and distal extremities, said distal extremity of the outer flexible elongate tubular member being secured to the first end of said expansion member and an inner flexible elongate tubular member having proximal and distal extremities, said distal extremity of the inner flexible elongate tubular member being secured to the second end of said expansion member.

12. A device as recited in claim 11 wherein said second dimension is greater than said first dimension.

13. A device as recited in claim 11 wherein said expansion member comprises a first plurality of flexible elongate elements helically wound around the longitudinal axis of said expansion member.

14. A device as recited in claim 11 further comprising a second plurality of flexible elongate elements disposed coaxially with said first plurality of flexible elongate elements, and wherein said first plurality of flexible elongate elements has a first direction of rotation and said second plurality of flexible elongate elements has a second direction of rotation.

15. A device as recited in claim 11 further comprising a means for maintaining said prosthesis in a fixed position on said expansion member prior to deployment within said body passageway.

16. A method for intraluminal delivery and deployment of an expandable stent or prosthesis within a body passageway which comprises the steps of:

placing said stent or prosthesis over an expansion member, said expansion member being moveable between a first configuration wherein said member is defined by a first dimension extending in a radial direction, and a second configuration wherein said member is defined by a second dimension extending in said radial direction;

advancing said expansion member, with said prosthesis engaged upon, to a predetermined site in the body passageway; and applying coaxially opposed forces on said expansion member in an axial direction to move said expansion member between said first configuration to said second configuration wherein said expansion member exerts radial force on said prosthesis and said prosthesis is expanded and implanted into said predetermined site.

17. A method as recited in claim 16 which further comprises the step of positioning a guidewire in the body passageway, and wherein said advancing step is accomplished by threading said expansion member over said guidewire.

18. A method for further expanding a stent or prosthesis previously deployed in a predetermined site within a body passageway which comprises the steps of:

advancing an expansion member to said predetermined site, said expansion member being moveable between a first configuration wherein said member is defined by a first dimension extending in a radial direction, and a second configuration wherein said member is defined by a second dimension extending in said radial direction; and applying opposed forces on said expansion member in an axial direction to move said expansion member between said first configuration to said second configuration wherein said expansion member exerts radial force on said prosthesis and said prosthesis is further expanded and implanted into said predetermined site.

19. A method as recited in claim 18 which further comprises the step of positioning a guidewire in the body passageway, and wherein said advancing step is accomplished by threading said expansion member over said guidewire.

* * * * *